US007963143B2

(12) United States Patent
Baumann et al.

(10) Patent No.: US 7,963,143 B2
(45) Date of Patent: Jun. 21, 2011

(54) PROCEDURE FOR OPERATING A PARTICLE SENSOR THAT IS ARRANGED DOWNSTREAM AFTER A PARTICLE FILTER AND DEVICE FOR IMPLEMENTING THIS PROCEDURE

(75) Inventors: Thomas Baumann, Kornwestheim (DE); Enno Baars, Leonberg (DE); Harald Koehnlein, Stuttgart (DE); Herbert Schumacher, Gerlingen (DE); Bernhard Kamp, Ludwigsburg (DE)

(73) Assignee: Robert Bosch GmbH, Stuttgart (DE)

( * ) Notice: Subject to any disclaimer, the term of this patent is extended or adjusted under 35 U.S.C. 154(b) by 495 days.

(21) Appl. No.: 12/120,559

(22) Filed: May 14, 2008

(65) Prior Publication Data

US 2009/0013758 A1 Jan. 15, 2009

(30) Foreign Application Priority Data

May 14, 2007 (DE) .......................... 10 2007 022 590

(51) Int. Cl.
*G01N 3/62* (2006.01)
(52) U.S. Cl. ..................................... 73/1.01; 73/514.25
(58) Field of Classification Search .................. 73/1.01, 73/514.25
See application file for complete search history.

(56) References Cited

U.S. PATENT DOCUMENTS

| 6,076,389 A | 6/2000 | Kaneko |
| 7,546,762 B2 * | 6/2009 | Zhang ........................ 73/114.76 |

FOREIGN PATENT DOCUMENTS

| DE | 41 39 325 | 1/1993 |
| DE | 101 33 384 | 1/2003 |
| DE | 102 39 610 | 6/2004 |
| DE | 10 2005 034 247 | 1/2007 |
| DE | 10 2006 018 956 | 10/2007 |
| EP | 1 624 166 | 8/2006 |

* cited by examiner

*Primary Examiner* — Hezron Williams
*Assistant Examiner* — Rodney T Frank
(74) *Attorney, Agent, or Firm* — Merchant & Gould P.C.

(57) ABSTRACT

A procedure for operating a particle sensor that is arranged downstream after a particle filter, at which an ash contamination can occur, and a device for implementing the procedure, are suggested. A remaining operating time determination determines the remaining operating time of the particle sensor related to an ash contamination. Alternatively or additionally the remaining operating time determination provides a correction signal, with which the sensitivity loss of the particle sensor caused by the ash contamination can be considered.

17 Claims, 1 Drawing Sheet

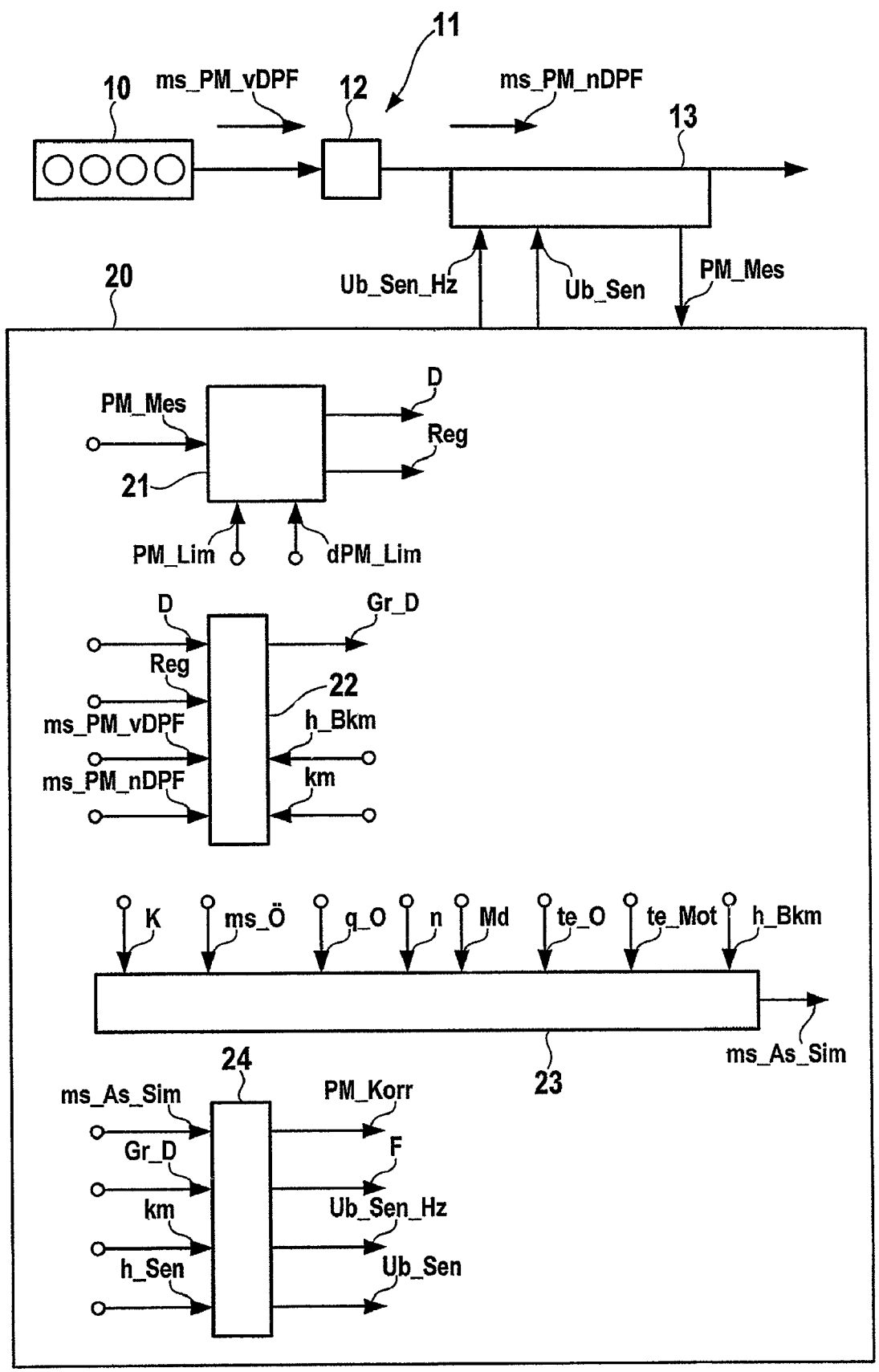

PROCEDURE FOR OPERATING A PARTICLE SENSOR THAT IS ARRANGED DOWNSTREAM AFTER A PARTICLE FILTER AND DEVICE FOR IMPLEMENTING THIS PROCEDURE

TECHNICAL FIELD

The invention is based on a procedure for operating a particle sensor that is arranged downstream after a particle filter and on a device for implementing the procedure according to the category of the independent claims.

Subject matter of the invention is furthermore a control program as well as a control program product.

For controlling and if necessary regulating the combustion features during combustion processes there is a demand for detecting at least a measure for the particle concentration in the exhaust gas. There is especially a demand for detecting at least a measure for the particle concentration in the exhaust gas of combustion engines, particularly diesel-combustion engines.

BACKGROUND

In DE 101 33 384 A1 a particle sensor is described, in which the electrodes are interlocked with one another in an alternating comb-like manner and which can be termed interdigital-electrodes. The impedance and/or its variation between the two electrodes can at least be used as a measure for the particle mass, which occurred in a preset time and/or related to the driving distance a of a motor vehicle, in which a combustion engine is used as a drive. Because the measuring effect is based on an accumulation of particles, the particle sensor can be termed collecting particle sensor.

DE 10 2005 034 247 A1 describes a procedure for controlling an exhaust gas threshold value of a combustion engine by use of a controller, which evaluates the signal of at least one exhaust gas sensor and provides an error signal if an exhaust gas threshold value is exceeded. Thereby the emission of the combustion engine that has been calculated for the present driving status is detected by use of a model of the combustion engine and compared to the signal of the exhaust gas sensor or a reference value that has been deduced from it. The exhaust gas sensor can be a particle sensor that is arranged downstream after the particle filter. For evaluating, if the particle filter is defect, the quotient of the measure for the particle current, which has been determined by the particle sensor, and of the calculated particle emission is build and compared to a threshold value.

DE 10 2006 018 956 A1 describes a procedure for determining a particle mass or a particle mass current in a flue of a combustion engine by use of a particle sensor, whereby the detected signal variation is compared to an anticipated signal variation that has been calculated by use of a combustion engine model. Thereby it is provided that the detected signal variation of the particle sensor and/or the calculated anticipated signal variation of the particle sensor are corrected considering the influence factors on the cross sensitivity of the particle sensor. Therefore the efficiency of the particle filter can be determined comparably exactly with the pre-known procedure even during dynamic processes.

A collecting particle sensor collects not only the particles that have to be detected, but also the ash that is contained in the exhaust gas. While the particles that have to be detected can be eliminated within a regeneration by heating the section of measurements of the particle sensor up to a free-burn temperature, the ash that has condensed on the section of measurements cannot be eliminated offhand. But also on the section of measurements of a non-collecting particle sensor an ash condensation can occur, which affects the measuring signal. Due to the ash contamination the remaining operating time of the particle sensor is limited to a value, at which the sensitivity towards the particles that have to be detected falls under a preset measure.

The invention is based on the task, to provide a procedure for operating a particle sensor that is arranged downstream after a particle sensor and a device for implementing this procedure, with which the particle sensor can be operated as long as possible despite the impact of ash, which can occur especially at a defect of the particle filter.

This task is solved by the specified characteristics in the independent claims.

SUMMARY

The way of proceeding according to the invention has the advantage that the particle sensor can be operated as long as possible before a replacement is required despite the impact of ash, which occurs at a semi-permeable particle filter already at the activation of a new particle filter and at an almost impermeable particle filter not until a defect of the particle filter occurs.

At a semi-permeable particle filter after the first activation and at an almost impermeable particle filter after the detected defect of the particle filter a remaining operating time-determination is provided, which determines the remaining operating time of the particle filter regarding the ash contamination and/or which provides a correction signal, with which the sensitivity-decrease that is dependent on the ash contamination can be considered.

With the provided measures according to the invention the operating time of the particle sensor can be maintained despite an ash contamination until a criterion, especially one that is set by legislation, is reached without having to replace the particle sensor. Furthermore the measuring accuracy of the particle sensor can be substantially maintained during the remaining operating time. Altogether a cost efficiency results by avoiding an early replacement of the particle sensor.

Advantageous embodiments and improvements according to the invention's procedure arise from dependent claims.

One embodiment provides a comparison of the particle sensor measuring signal with an absolute-threshold or with a gradient-threshold, whereby the remaining operating time of the particle sensor is determined not until after reaching a threshold.

One embodiment provides that the remaining coefficient of the particle filter is considered as a defect-dimension during the determination of the remaining operating time. The coefficient can be determined for one thing according to the procedure known from the state of the art mentioned in the beginning. For another thing it is possible to determine the coefficient of the particle filter at least approximately by use of a measuring signal that is provided by the particle sensor related to the operating time of the combustion engine, in whose exhaust gas area the particle sensor is arranged and/or related to the driving distance that a motor vehicle, in which the combustion engine is provided as a drive, has covered.

One embodiment provides that the remaining operating time determination considers the ash emission that has been emitted by the combustion engine, which is determined by use of an ash-model of the combustion engine. The ash-model can be a measure for the oil consumption and/or the oil quality and/or the oil temperature and/or the engine speed and/or the load and/or the temperature and/or the entire operating time of the combustion engine.

The remaining operating time of the particle sensor can alternatively or additionally be estimated on the basis of the entire operating time of the particle sensor and/or on the basis of the driving distance that has been covered by the motor vehicle.

An improvement provides that during the remaining operating time determination within the scope of a partially defect particle filter an operating voltage of the sensor distance of the particle sensor is minimized or completely switched off, in order to minimize the ash accretion. Alternatively or additionally it can be provided that during the remaining operating time determination the sensor distance of the particle sensor is heated, whereby the temperature is preferably defined to a value, which is above the exhaust gas temperature.

According to the invention the device for implementing the procedure firstly concerns a controller, which is customized for implementing the procedure. Preferably the controller is customized as a sensor-controller, which preferably contains at least the remaining operating time determination. The separation between the sensor-controller and a motor-controller has the advantage that in the case of a required replacement of the motor-controller the already determined remaining operating time is still available. The controller contains preferably at least one electronic memory, in which the procedure steps are displayed as a control program.

According to the invention the control program provides that all steps of the procedure according to the invention are performed when it runs in a controller.

According to the invention the control program product with a program code that is stored on a machine readable medium performs the procedure according to the invention when the program runs in a controller.

Further advantageous improvements and embodiments according the invention's procedure arise from further dependent claims. Embodiments of the invention are shown in the drawing and further explained in the following description.

BRIEF DESCRIPTION OF THE DRAWINGS

The FIGURE shows a technical environment, in which a procedure for operating a particle sensor that is arranged downstream after a particle filter is running according to the invention.

The FIGURE shows a combustion engine 10, in whose exhaust gas area 11 a particle filter 12 and a particle sensor 13 that is behind the particle filter 12 are arranged. In the exhaust gas area 11 a particle emission ms_PM_vDPF of the combustion engine 10 occurs upstream before the particle filter 12 and a particle slip ms_PM_nDPF downstream after the particle filter 12. The particle sensor 13 provides a particle measurement signal PM_Mes for the controller 20. The controller 20 contains a measurement signal assessment 21, a defect intensity determination 22, an ash model 23 as well as a remaining operating time determination 24. The controller provides a sensor heating voltage Ub_Sen_Hz as well as sensor operating voltage Ub_Sen for the particle sensor 13.

Due to the incomplete combustion processes a particle emission ms_PM_vDPF can occur during the operation of the combustion engine 10, which are filtered out from the exhaust gas by the particle filter 12 as an unwanted off-gas stream component.

The particle filter 12 can be arranged for example as a ceramic filter or a sinter metal filter, which has an efficiency of almost 100%, in other words is almost impermeable in a proper operating status. The particle filter 12 can furthermore be arranged as a partially permeable particle filter 12, at which at least a minimal particle slip ms_PM_nDPF constantly occurs.

The particle sensor 13 that is arranged downstream after the particle filter 12 allows especially a diagnosis of the particle filter 12 by an assessment of the particle slip ms_PM_nDPF, which is provided to the controller 20 by the particle sensor 13 as a particle measurement signal PM_Mes.

The measurement signal assessment 21 checks the particle sensor measurement signal PM_Mes for an exceeding of an absolute threshold value PM_Lim and/or for an exceeding of a gradient threshold value dPM_Lim. The absolute threshold value PM_Lim is only exceeded in a particle filter 12, which has an efficiency of almost 100%, if a defect of the particle filter 12 has occurred. By use of an assessment of the increase of the particle measurement signal PM_Mes based on a basic parameter, in other words a gradient assessment, it can be differentiated especially at a semi-permeable particle filter 12 between a proper functioning particle filter 12 and one with a beginning defect, at which the efficiency falls below the expected value in a proper operating status of the particle filter 12.

The measurement signal assessment 21 provides a defect signal D when one of the threshold values PM_Lim, dPM_Lim is exceeded. Furthermore the measurement signal assessment 21 can provide a regeneration signal Reg, which causes a regeneration of a particle sensor 13 that is arranged as a collecting particle sensor. At a semi-permeable particle filter 12 regeneration processes of the particle sensor 13 occur during the normal operation of the particle filter 12. At a particle filter 12 with an efficiency of almost 100% regeneration processes usually occur only after the appearance of the defect signal D.

At a semi-permeable particle filter 12 particle slip ms_PM_nDPF occurs already at the activation. At an almost impermeable particle filter 12 a considerable particle slip ms_PM_nDPF occurs only at an at least partially defect particle filter 12. The particle slip ms_PM_nDPF contains on the one hand the particles that have to be detected by the particle sensor 13, but on the other hand ash, which originates for example from the combustion of the fuel and its additives that has been added to the combustion engine 10 and especially from the combustion of engine oil in the combustion engine 10. Because the particle sensor 13 accumulates independently of the sensor concept not only the particles that have to be detected in general but also the ash that is contained in the exhaust gas, from which the particle sensor 13 cannot be regenerated anymore, it has to be counted on an ash contamination of the particle sensor 13. Due to the increasing ash contamination the increasing impact of the particle sensor 13 with ash limits the remaining operating time of the particle sensor 13, which is determined by the remaining operating time determination 24.

The remaining operating time determination 24 determines the remaining time of the particle sensor 13 at a semi-permeable filter already after the first activation of the particle filter 12 or the particle sensor 13. At an almost impermeable particle filter it is preferably provided that the remaining operating time of the particle sensor 13 is determined by the remaining operating time determination 24 only after an established defect of the particle filter 12.

Independent of the arrangement of the particle filter 12 and despite an occurred defect of the particle filter 12 a further operation of the particle filter 12 can be provided, if the defect lies within a reliable range, which can be appointed by the exhaust gas legislation.

In the case that the particle filter 12 can be still operated despite an occurred defect, the remaining operating time determination 24 considers the defect intensity Gr_D, which is provided by the defect intensity determination 22.

The defect intensity determination 22 determines the defect intensity Gr_D after the occurrence of the defect signal D for example depending on the frequency of the regeneration processes, which can be caused by the regeneration signal Reg. Alternatively or additionally the defect intensity Gr_D can be estimated by means of the entire combustion engine operating time h_Bkm and/or by means of the passed driving distance of a motor vehicle, in which the combustion engine 10 is used as the impetus. Alternatively or additionally the defect intensity Gr_D can be estimated from the remaining efficiency of the particle filter 12, which can be determined for example by means of the particle slip ms_P-M_nDPF in relation to the particle emission ms_PM-vDPF. The determination of the particle filter efficiency can be inferred from the state of the art that has been mentioned at the beginning, which has been always referred to completely.

The ash model 23 determines the calculated ash emission s_As_Sim for example by means of a fuel signal K, which mirrors the fuel type as for example a benzine/ethanol mixture, bio-diesel etc. and/or by means of a measure ms_O for the oil consumption that has been detected from the signal of an oil fill level sensor and/or depending on the oil temperature te_O and/or depending on the oil quality q_O that has been detected by the oil quality sensor and/or depending on the engine speed n and/or the load Md and/or depending on the temperature te_Mot and/or depending on the entire operating time h_Bkm as a measure for the increase of the oil consumption of the combustion engine 10 due to wear.

The remaining operating time determination 24 determines the remaining operating time of the particle sensor 13 with regard to the ash contamination for example by means of an integration of the calculated ash emission ms_As_Sim, which is weighted with the probably present defect intensity Gr_D. At a higher probably present defect intensity Gr_D it has to be counted on a shorter remaining operating time of the particle sensor 13 due to the higher ash contamination related to a basic parameter as for example time or driving distance. Alternatively or additionally the remaining operating time determination 24 can estimate the remaining operating time of the particle sensor 13 from the entire operating time h_Sen of the particle sensor 13 and/or from the driving distance km that has been covered by the motor vehicle.

In an extreme case the remaining operating time determination 24 determines the remaining operating time of the particle sensor 13 without further incoming signals only by means of the detected operating time of the particle sensor 13, whereby it is assumed that the maximally possible operating time of the particle sensor 13 is preset.

The remaining operating time determination 24 determines alternatively or preferably additionally a particle correction signal PM_Korr, with which the sensitivity of the particle sensor 13 is corrected for example by adjusting the assessment of the particle sensor measuring signal PM_Mes. Thereby the measure for the momentary particle stream or for the particles that occur in a time interval can be determined comparably accurate from the particle sensor measuring signal PM_Mes during the remaining operating time despite the occurring ash contamination. The remaining operating time determination 24 provides furthermore alternatively or additionally a fault signal F when reaching an operating time threshold value, which can be displayed to an operator of the combustion engine 10 and/or stored in a fault recorder.

Alternatively or additionally the remaining operating time determination 24 can take measures during the remaining operating time of the particle sensor 13, which reduce the accumulation of ash in order to extend the remaining operating time of the particle sensor 13. The measures can also be initiated otherwise so that the remaining operating time detector 24 only notices the measures and then considers them when detecting the remaining operating time of the particle sensor 13. A first measure for example provides a constant heating of the particle sensor 13 with the sensor voltage Ub_Sen_Hz also outside of regeneration processes to the operating temperature, which preferably lies above the exhaust gas temperature in the area of the particle sensor 13. By the resulting thermophoretic effect the accumulation of ash is reduced.

A further measure provides for example the reduction of the sensor operating voltage Ub_Sen of a resistive particle sensor 13 with for example inter digital electrodes. By the reduction of the polarizing influence or the reduction of the gravitational force from already polarized/electrically loaded ash the accumulation of ash is also reduced.

The invention claimed is:

1. A method of operating a particle sensor arranged downstream after a particle filter wherein an ash contamination of the particle sensor can occur, the method comprising:
   determining a remaining operating time of the particle sensor related to the ash contamination via a remaining operating time determination, whereby a correction signal is provided such that a sensitivity loss of the particle sensor due to the ash contamination is considered.

2. A method according to claim 1, wherein determining includes determining the remaining operating time of the particle sensor from a first activation of the particle sensor.

3. A method according to claim 1, wherein determining includes determining after a detection of a particle filter defect, wherein an assessment of a particle sensor-sensor signal is used to detect the particle filter defect.

4. A method according to claim 3, wherein the assessment includes a comparison of the particle sensor-sensor signal with an absolute threshold value and/or a gradient threshold value.

5. A method according to claim 1, further comprising determining an efficiency of the particle filter by the remaining operating time determination as a defect intensity.

6. A method according to claim 5, wherein determining an efficiency includes:
   a) determining by a particle sensor measuring signal related to an entire operating time of a combustion engine, wherein the particle filter and the particle sensor are arranged in an exhaust gas area of the combustion engine and relating to a driving distance that has been covered by a motor vehicle, wherein the motor vehicle provides a combustion engine as a drive.

7. A method according to claim 5, wherein determining an efficiency includes determining via a particle sensor measuring signal and an ash emission of the combustion engine that has been calculated by an ash model.

8. A method according to claim 1, wherein determining includes considering an ash emission of a combustion engine that has been determined by means of an ash model.

9. A method according to claim 8, wherein the ash model considers at least:
   a) a fuel type of the combustion engine;
   b) a measure of an oil consumption of the combustion engine;
   c) an oil quality of the combustion engine;
   d) a load of the combustion engine;

e) a temperature of the combustion engine; and f) an entire operating time of the combustion engine.

10. A method according to claim 1, wherein determining includes considering an entire operating time of the particle sensor or the driving distance that has been covered by a motor vehicle, wherein the drive of the motor vehicle is a combustion engine, wherein a particle filter and the particle sensor are arranged in the exhaust gas area of the combustion engine.

11. A method according to claim 1, further comprising at least partially minimizing an operating voltage of the particle sensor in order to minimize an ash accumulation.

12. A method according to claim 1, wherein the particle sensor is provided at least temporally with a sensor heating voltage in order to minimize an ash accumulation.

13. A device, comprising:
a customized controller constructed and configured to operate a particle sensor arranged downstream after a particle filter, wherein an ash contamination of the particle sensor can occur, and to determine a remaining operating time of the particle sensor related to the ash contamination via a remaining operating time determination, whereby a correction signal is provided such that a sensitivity loss of the particle sensor due to the ash contamination is considered.

14. A device according to claim 13, wherein at least one customized controller is provided additionally to a combustion engine controller as a separate sensor controller, wherein the sensor controller contains at least a remaining operating time determination.

15. A device according to claim 14, wherein the at least one controller contains a measuring signal assessment, a defect intensity determination and an ash model.

16. A computer-implemented method for operating a particle sensor arranged downstream after a particle filter, wherein an ash contamination of the particle sensor can occur, the computer-implemented method comprising the step of: determining a remaining operating time of the particle sensor related to the ash contamination via a remaining operating time determination, whereby a correction signal is provided such that a sensitivity loss of the particle sensor due to the ash contamination is considered.

17. A computer program product with a program code stored on a machine readable device and executed on a customized controller, for operating a particle sensor arranged downstream after a particle filter, wherein an ash contamination of the particle sensor can occur, the program code including instructions for determining a remaining operating time of the particle sensor related to the ash contamination via a remaining operating time determination, whereby a correction signal is provided such that a sensitivity loss of the particle sensor due to the ash contamination is considered.

* * * * *